(12) United States Patent
Cook et al.

(10) Patent No.: US 7,883,701 B2
(45) Date of Patent: Feb. 8, 2011

(54) METHOD FOR ENHANCING GROWTH OR INCREASING FEED EFFICIENCY THROUGH REDUCING BINDING BETWEEN ENDOTOXIN AND ITS RECEPTOR IN THE GASTROINTESTINAL TRACT

(75) Inventors: Mark E. Cook, Madison, WI (US); Mingder Yang, Madison, WI (US); David M. Barnes, Oregon, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 935 days.

(21) Appl. No.: 10/741,611

(22) Filed: Dec. 19, 2003

(65) Prior Publication Data

US 2005/0136052 A1 Jun. 23, 2005

(51) Int. Cl.
  *A61K 39/40* (2006.01)
  *A61K 39/00* (2006.01)
(52) U.S. Cl. .................................. 424/139.1; 424/184.1
(58) Field of Classification Search .................. None
  See application file for complete search history.

(56) References Cited

U.S. PATENT DOCUMENTS

| 5,989,584 A | 11/1999 | Cook et al. |
| 6,213,930 B1 | 4/2001 | Cook |

FOREIGN PATENT DOCUMENTS

WO WO 00/53224 * 9/2000

OTHER PUBLICATIONS

Mikayama et al. PNAS, 1993. 90: 10056-10060.*
Burgess et al ., J Cell Biol. 111:2129-2138, 1990.*
Lazar et al. Mol Cell Biol. 8:1247-1252, 1988.*
Cario et al ., J of Immunology, 2000, V.164, pp. 966-972).*
Christopher D. Raeburn, et al. Toll-like receptors and *surgical disease*. Surgery. May 2002; 131(5):477-483.
Maria T. Abreu, et al. Decreased expression of *Toll-like receptor-4 and MD-2 correlates* with intestinal epithelial cell protection against dysregulated proinflammatory gene expression in response to bacterial lipopolysaccharide. J Immunol. Aug. 1, 2001;167(3)1609-1616.
Masaya Kobayashi, et al. Toll-like receptor-dependent production of IL-12p40 causes chronic enterocolitis in myeloid cell-specific Stat3-deficient mice. J Clin Invest. May 2003;111(9):1297-308.
Joel D. Schilling, et al. Toll-like receptor 4 on stromal and hematopoietic cells mediates innate resistance to uropathogenic *Escherichia coli*. Proc Natl Acad Scl U S A. Apr. 1, 2003;100(7):4203-8. Epub Mar. 24, 2003.
Elke Cario, et al. Lipopolysaccharide activates distinct signaling pathways in intestinal epithelial cell lines expressing Toll-like receptors. J Immunol. Jan. 15, 2000;164(2):966-72.
Sabroe, L.C. Parker, et al. Toll-like receptors: their role in allergy and non-allergic inflammatory disease. Clin Exp Allergy. Jul. 2002;32(7):984-9. Review.
David P. Funda, et al. CD14 is expressed and released as soluble CD14 by human intestinal epithelial cells in vitro: lipopolysaccharide activation of epithelial cells revisited. Infection and Immunity. Jun. 2001; p. 3772-3781.
Sandhia Naik, et al. Absence of Toll-like receptor 4 explains endotoxin hyporesponsiveness in human intestinal epithelium. J Pediatr Gastroenterol Nutr. Apr. 2001;32(4):449-53.
Ruemmele FM, et al. Lipopolysaccharide modulation of normal enterocyte turnover by toll-like receptors is mediated by endogenously produced tumour necrosis factor alpha. Gut. Dec. 2002;51(6);842-8. Erratum in: Gut Jan. 2003;52(1):157.
Daniel Hwang. Modulation of the expression of cyclooxygenase-2 by fatty acids mediated through toll-like receptor 4-derived signaling pathways. FASEB J. Dec. 2001;15(14):2556-64. Review.

* cited by examiner

*Primary Examiner*—Michail A Belyavskyi
(74) *Attorney, Agent, or Firm*—Quarles & Brady LLP

(57) ABSTRACT

A method for reducing gastrointestinal inflammation, enhancing growth, or improving feed efficiency in a human or non-human animal is disclosed. The method involves administering to the animal an agent that can reduce the formation of the signal transduction complex of endotoxin, TLR4 and CD14 on the cellular surface of a cell in the gastrointestinal tract of the animal. In a preferred embodiment, an antibody against the extracellular domain of TLR4 or CD14 is used to reduce the formation of the complex. A composition that contains the antibody and an ingestible carrier is also disclosed. Further disclosed is a method for producing a peptide for enhancing growth, improving feed efficiency, or both in a human or non-human animal.

17 Claims, No Drawings

SEQUENCE LISTING

<160> NUMBER OF SEQ ID NOS: 2

<210> SEQ ID NO 1
<211> LENGTH: 20
<212> TYPE: PRT
<213> ORGANISM: Artificial
<220> FEATURE:
<223> OTHER INFORMATION: synthetic peptide

<400> SEQUENCE: 1

Lys Arg Val Asp Ala Asp Ala Asp Pro Arg Gln Tyr Ala Asp Thr Val
1               5                   10                  15

Lys Ala Leu Cys
            20

<210> SEQ ID NO 2
<211> LENGTH: 20
<212> TYPE: PRT
<213> ORGANISM: Artificial
<220> FEATURE:
<223> OTHER INFORMATION: synthetic peptide

<400> SEQUENCE: 2

Glu Leu Asp Asp Glu Asp Phe Arg Cys Val Cys Asn Phe Ser Glu Pro
1               5                   10                  15

Gly Pro Asp Trp
            20

METHOD FOR ENHANCING GROWTH OR INCREASING FEED EFFICIENCY THROUGH REDUCING BINDING BETWEEN ENDOTOXIN AND ITS RECEPTOR IN THE GASTROINTESTINAL TRACT

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to a method for enhancing growth or improving feed efficiency in a human or non-human animal by reducing the binding between bacterial endotoxin and its cellular receptors in the gastrointestinal tract of the animal.

Enhancing animal growth or feed efficiency, can have substantial impact on, for example, the animal meat industry by reducing the high cost of feeding food-producing animals and directly improving profitability. For example, in the poultry industry, even a slight increase in broiler growth rate coupled with reduced feed consumption brings the broiler to market maturity faster at lower cost. With approximately eight billion broilers raised annually in the United States, significant savings are realized.

In animals, the gastrointestinal tract performs the function of digesting food and absorbing nutrients for the growth and other needs of the animals. The gastrointestinal tract is the primary residing place for the endogenous bacterial flora that include both gram-positive and gram-negative bacteria. Exogenous pathogenic bacteria also gain access to the gastrointestinal tract quite frequently. These bacteria can induce inflammatory responses in the gastrointestinal tract which increase tissue damage, cause the thickening of the gut wall, and negatively affect the ability of the animals, particularly mammals and avians, to efficiently digest food and absorb and use nutrients for growth.

Endotoxin, the bacterial lipopolysaccharide (LPS), is a characteristic outer membrane entity of gram-negative bacteria and a potent inducer of inflammatory responses. Although the exact mechanism on how endotoxin induces gastrointestinal inflammation is not clear, recent evidence suggests that endotoxin binds to receptors on host cells and the binding leads to the release of inflammatory mediators and activation of immune cells. Recent evidence further suggests that toll-like receptor 4 (TLR4) and CD14 act together as the cellular receptor for endotoxin to transduce signals. The association of MD2 to TLR4 may also be necessary in this regard. Endotoxin is shepherded to CD14 by LPS-binding protein (LBP). When bound by endotoxin, CD14 recruits and activates TLR4-MD2 complex to induce a cascade of downstream events that lead to inflammation responses. Since CD14 does not have a cytoplasmic domain, it relies on the cytoplasmic domain of TLR4 to transduce signals.

Reducing gastrointestinal inflammation can alter animal feeding behavior and improving animal health. Phospholipase $A_2$ is an enzyme that is involved in the production of prostaglandins and leukotrienes, two important factors for causing gastrointestinal inflammation. U.S. Pat. Nos. 6,213,930 and 6,383,485 disclosed that feeding animals with anti-phospholipase $A_2$ antibodies can reduce gastrointestinal inflammation, enhance animal growth and improve feed efficiency.

Although many studies have suggested that endotoxin from gram-negative bacteria induces inflammatory responses through binding to its cellular receptors, it is not clear whether reducing the binding in the gastrointestinal tract of an animal can reduce gastrointestinal inflammation, alter animal feeding behavior and improve animal health.

BRIEF SUMMARY OF THE INVENTION

The present invention is summarized in that gastrointestinal inflammation is reduced, resulting in improved gut health (less inflammation), enhanced growth and increased feed efficiency in a human or non-human animal by administering to the animal an agent that can reduce the formation of the signal transduction complex of endotoxin, TLR4 and CD14 on the cellular surface of a cell in the gastrointestinal tract of the animal.

The present invention would be beneficial to the animal meat industry and the aquaculture industry. The present invention would also be beneficial to humans who are underweight, have eating disorders or have problems maintaining their weight.

In a preferred embodiment of the invention, the enhancement in growth, the improvement in feed efficiency, or both are achieved by feeding an antibody against the extracellular domain of TLR4 or CD14 to a human or non-human animal. A composition that contains the antibody and an ingestible carrier is also within the scope of the invention.

In a related aspect, the present invention is a method for producing a peptide for enhancing growth, improving feed efficiency, or both in a human or non-human animal. The method involves administering an anti-cell-surface-receptor antibody into the gastrointestinal tract of an animal and determining whether the growth, feed efficiency, or both of the animal are enhanced. If the growth, feed efficiency, or both are enhanced, one can produce a soluble peptide from the extracellular or ligand binding domain of the receptor and use the peptide to compete with the receptor for binding to a ligand of the receptor. As a result, growth can be enhanced and feed efficiency can be improved.

BRIEF DESCRIPTION OF THE SEVERAL VIEWS OF THE DRAWINGS

Not applicable.

DETAILED DESCRIPTION OF THE INVENTION

Endotoxin is believed to cause gastrointestinal inflammation by binding to its cellular receptors and forming a signal transduction complex with TLR4 and CD14, through which signals are transduced for eliciting inflammatory responses. It is disclosed here that by interfering with the formation of the signal transduction complex, one can reduce gastrointestinal inflammation and enhance growth and feed efficiency. During normal food digestion, stimulation of intestinal smooth muscle is reduced, and more efficient feed conversion and bodily growth can be achieved. During gastrointestinal trauma, such as colitis and necrosis, inflammation is reduced and further damage can be avoided. The present invention can also be used to treat inflammatory bowel disease, which is characterized by chronic intestinal inflammation caused by bacteria. In the Example described below, the inventors generated antibodies to TLR4 and CD14 as tools for blocking the formation of the signal transduction complex of endotoxin, TLR4 and CD14. Using chickens as an example, the inventors demonstrated that feeding these antibodies to the animals resulted in enhanced growth, improved feed efficiency, or both.

In one aspect, the present invention relates to a method for reducing gastrointestinal inflammation, enhancing growth or improving feed efficiency in a human or non-human animal through administering to the animal an agent that can reduce the formation of the signal transduction complex of endotoxin, TLR4 and CD14 on the cellular surface of a cell in the gastrointestinal tract of the animal. By enhancing growth, we mean that for a selected period of time (e.g., one week, two weeks, three weeks or a longer period of time such as eight weeks), animals administered with the agent gain more weight than control animals. Feed efficiency is defined as the amount of feed in grams required to cause an animal to gain 1 gram of weight. A 100 point improvement in feed efficiency corresponds to a decrease of 1 gram in the amount of feed required to cause the animal to gain 1 gram. The term "feed conversion" or "feed conversion efficiency" is used interchangeably with the term "feed efficiency." The present invention can be practiced on any human or non-human animal. Preferably, the present invention is practiced on fish, avian and mammalian animals. Preferred avian animals include chickens, pheasants, ducks, turkeys, quail and geese. Preferred mammalian animals include bovine, ovine, porcine, caprine, rodent and human animals.

In a preferred embodiment of the present invention, the formation of the signal transduction complex of endotoxin, TLR4 and CD14 is reduced by an antibody to the extracellular domain of TLR4 or CD14. It is not known whether endotoxin (shepherded by LBP) binds directly only to CD14 or to both CD14 and TLR4, or whether CD14 and TLR4 form a dimer first before binding to endotoxin or endotoxin binds to CD14 first and later recruits TLR4 into the complex. However, it is known that the end result of the binding is the formation of a complex by endotoxin, TLR4 and CD14 and this complex is necessary for the signal transduction that elicits inflammatory responses. It is also known that the extracellular domains of TLR4 and CD14 involved in the formation of the signal transduction complex (Hwang, D., FASEB J. 15:2556-2564, 2001; Raeburn, C.D. et al., Surgery 131:477-483, 2002). Thus, an antibody generated against the extracellular domain of TLR4 or CD14 can block the formation of the complex to achieve inflammation reduction, growth enhancement and feed efficiency improvement. Since LBP and MD2 are also required for the formation of the complex (Hwang, D., FASEB J. 15:2556-2564, 2001; Raeburn, C.D. et al., Surgery 131:477-483, 2002), an antibody to LBP or MD2 can also be used in the present invention.

Given that the amino acid sequences of TLR4, CD14, LBP and MD2 in various animal species are available in the art, it is well within the capability of a skilled artisan to generate monoclonal or polyclonal antibodies described above. In a preferred embodiment, antibodies in the egg yolks of an avian animal (e.g., chickens, pheasants, ducks, turkeys, geese and the like) are used (see e.g., U.S. Pat. Nos. 5,080,895, 5,989, 584 and 6,213,930, each of which is herein incorporated by reference in its entirety). The advantage of this is that eggs or egg yolks containing the antibodies can be mixed with a food or feed directly for oral consumption. No purification of the antibodies is necessary. Of course, it is possible to collect antibodies from whole blood, plasma or serum. Antibodies can also be collected from the milk of an inoculated cow or goat. Additionally, hybridoma and various other technologies can also be used to generate antibodies in the present invention.

As an alternative to administering an antibody produced by other animals or cells to a target animal as described above, the target animal can be made to generate suitable antibodies by itself through oral inoculation (vaccination), which is a familiar technology in the art (examples can be found in Strindelius L. et al., *Infection & Immunity* 70:1434-42, 2002; and Kidane A. et al., *Vaccine* 19:2637-46, 2001, both are herein incorporated by reference in their entirety). Immunogenic peptides derived from the extracellular domain of TLR4 or CD14, or from LBP or MD2 are suitable antigens for oral inoculation.

In addition, soluble peptides derived from the extracellular domain of TLR4 and CD14 can be used directly to compete with the intact proteins for forming a complex with endotoxin and thus block the formation of the signal transduction complex of endotoxin, TLR4 and CD14. The three peptides used in the example below for generating TLR4 and CD14 antibodies are such soluble peptides. The soluble peptide strategy disclosed here is equally applicable to other receptors. Based on the teaching of this disclosure, a skilled artisan can pick any cellular membrane receptor, make an antibody to its cellular binding domain or ligand binding domain, administer the antibody into the gastrointestinal tract of an animal, and determine whether growth, feed efficiency, or both of the animal are enhanced. If the answer is yes, then one can make soluble peptides from the extracellular or ligand binding domain of the receptor and administer the peptides into the gastrointestinal tract of the animal to enhance growth, improve feed efficiency, or do both. In a preferred embodiment, the peptides are produced in a transgenic animal or transgenic plant (e.g., alfalfa plant).

A skilled artisan can also use other strategies for reducing the formation of the signal transduction complex of endotoxin, TLR4 and CD14. For example, one can use various screening assays to identify agents that can interfere with the formation of the complex and use the agents identified in the present invention. The formation of the complex can also be reduced by reducing the amount or activity of TLR4, CD14, LBP or MD2 available for forming the complex. For example, the antisense technology can be used to reduce the amount of proteins and the recombinant DNA technology can be used to identify dominant negative proteins to inhibit the normal function of TLR4, CD14, LBP or MD2.

The agents that can be used in the present invention as described above can be administered by oral delivery or by injection, and is preferably administered in combination with a suitable carrier of the type commonly used in delivery of pharmaceuticals or nutritional supplements. Injection methods include, but are not limited to, subcutaneous, intraperitoneal, intramuscular, or intravenous injection. Oral administration, which is preferred, can include, but is not limited to, administration in tablet or powder form. Most preferably, the agent is fed directly by mixing with feed or by coating feed particles as described in U.S. Pat. No. 5,725,873, incorporated herein by reference in its entirety.

In a preferred method, antibodies are prepared as follows. A producer animal is immunized with a peptide or protein, such as a fragment of the extracellular domain of TLR4 or CD14, against which antibodies are desired so that the producer animal produces an antibody to said peptide or protein. A substance containing the antibody is obtained from said producer animal. The antibody can be subject to further purification if desired or can be used without further preparation in an animal feed. The method of Polson, A., M. B. von Wechmar and M. H. van Regenmortel, Isolation of viral IgY antibodies from yolks of immunized hens. Immunological Communications 9:475-493 (1980), incorporated herein by reference in its entirety, can be used to produce a preparation of egg-yolk antibodies. Laying hens can be inoculated with a fragment of the extracellular domain of TLR4 or CD14. Preferably, a suitable adjuvant is administered in conjunction with the hen inoculation to enhance the immunization. An adjuvant useful for this purpose is a water-in-oil emulsion adjuvant such as complete Freund's adjuvant. The extracellular fragment causes the hens to produce anti-TLR4 or anti-CD14 antibodies which are passively transferred into the egg yolk of eggs laid by the hens.

An egg preparation, e.g., egg yolks or whole eggs, containing the anti-TLR4 or anti-CD14 antibody can be collected and homogenized to form an emulsion. The resulting emulsion can be dried to form a powder containing the antibody. This powder can then be formulated in a manner appropriate to the administration route and then administered to the desired animals using methods known in the art. The preparation is preferably administered orally, most preferably as a supplement to the animal's diet.

The present invention is advantageous over what is currently being used in the poultry and livestock industries. Antibiotics are currently used in the commercial animal industry in order to increase food efficiency and weight gain. However, antibiotics leave a drug residue in the animal's tissue. Therefore, the animal must go through "withdrawal time." Withdrawal time is an amount of time sufficient for the antibiotic to clear animal tissues. During withdrawal time, the animal cannot be slaughtered for human consumption. Additionally, any eggs or milk produced cannot be utilized for human use. This precaution is utilized because of the concern that human consumption of milk with traces of penicillin, for example, will cause increase resistance to antibiotics in man, eventually rendering the use of antibiotics to fight bacterial diseases useless.

Secondly, the use of antibiotics over a long period of time can potentially cause an increased number of microorganisms able to infect an animal because these organisms slowly gain resistance due to constant exposure to the antibiotic. Thus, future bacterial diseases will be difficult if not impossible to treat.

EXAMPLE

Materials and Methods

Peptide source—The two peptides used for generating antibodies against CD14 were $NH_2$—KRVDADADPRQY-ADTVKALC—COOH (named CD14a, SEQ ID NO:1) and $NH_2$—ELDDEDFRCVCNFSEPGPDW—COOH (named CD14b, SEQ ID NO:2). The peptide used to generate antibodies against TLR4 was $NH_2$—FKEIRHKLTLRNN-FDLSLNVMKTC—COOH (named TLR4a, SEQ ID NO:3). The peptides were part of the extracellular domain of CD14 and TLR4 and were synthesized by the University of Wisconsin Biotech Center (Madison, Wis.).

Egg yolk antibody production—CD14a, CD14b or TLR4a were each injected to five laying hens for egg yolk antibody production. Antigen was prepared by emulsifying equal volume of antigen solution (200 μg/ml) with Freund's adjuvant (Sigma). Each hen was injected a total of 1 ml emulsified antigen intramuscularly where four injections were given to both thighs and both breasts with 0.25 ml inoculums per injection. Freund's complete adjuvant was used in the first inoculation whereas Freund's incomplete adjuvant was used in the second injections. Second inoculation was one week after the first inoculation.

Birds were checked daily for morbidity and mortality. Egg production was also recorded daily. Eggs were collected starting at day 21 after the first inoculation. Eggs were then broken and yolk was collected and freeze-dried. The dried egg yolk was then hand ground and egg yolk powder was then used to feed chickens for growth trials.

Broiler chicks growth trial—Ross x Ross cockerel broiler chicks were purchased from Sunnyside hatchery (Beaver Dam, Wis.). One day old chicks were grouped as 5 birds per pen, 3 to 10 pens per treatment depending on experiment and pens were randomized in battery cages. Egg yolk powder was mixed into chick mash feed at the dose of 0.1 g/kg. Feed and water were provided ad lib. Body weights, feed consumption were recorded at day 1 and day 22 for measuring final body weight, body weight gain and feed conversion (feed/gain). Birds were checked twice daily and if a dead bird was found, it was weighted immediately and the body weight was added back for calculating the final feed conversion.

Results

Results from three independent experiments are shown in Table 1 below. In all experiments, antibodies to CD14 or TLR4 enhanced growth in the chicks. The antibodies also improved feed efficiency in most chicken groups treated with the antibodies.

TABLE 1

| | 3-week average body weight (g) | Body weight increase over control | Feed conversion (food consumed/ body weight gain) | Feed conversion improvement |
|---|---|---|---|---|
| Experiment 1 | | | | |
| Control | 2859.7 | | 1.45 | |
| CD14a | 2967.7 | 3.8% | 1.46 | |
| TLR4a | 3224.0 | 12.7% | 1.43 | 2 points* |
| Experiment 2 | | | | |
| Control | 2335.7 | | 1.55 | |
| CD14a | 2448.6 | 4.8% | 1.50 | 5 points |
| TLR4a | 2424.8 | 3.8% | 1.71 | |
| Experiment 3 | | | | |
| Control | 2229.0 | | 1.56 | |
| CD14a | 2349.1 | 5.4% | 1.48 | 8 points |
| CD14b | 2361.1 | 5.9% | 1.52 | 4 points |
| TLR4a | 2452.6 | 10.0% | 1.49 | 7 points |

*One point improvement equals to 0.01 reduction in feed conversion.

The present invention is not intended to be limited to the foregoing example, but to encompass all such modifications and variations as come within the scope of the appended claims.

We claim:

1. A method for enhancing growth, improving feed efficiency, or both in a human or non-human animal, the method comprising the step of:
    administering to the animal an agent that can reduce formation of a complex on cellular surface of a cell in the gastrointestinal tract of the animal wherein the complex comprises endotoxin, toll-like receptor 4 (TLR4) and CD14 and wherein the agent comprises a member selected from (i) an antibody to the extracellular domain of TLR4 or CD14 and (ii) a soluble peptide that can compete with TLR4 or CD14 to form a complex with endotoxin wherein the soluble peptide comprises said extracellular domain of TLR4 or CD14.

2. A method for enhancing feed efficiency, or both in a human or non-human animal, the method comprising the step of:
    administering to the animal an agent that can reduce formation of a complex on cellular surface of a cell in the gastrointestinal tract of the animal wherein the complex comprises endotoxin, toll-like receptor 4 (TLR4) and CD14 and wherein the agent comprises an antibody to the extracellular domain of TLR4 or CD14.

3. The method of claim 2, wherein the antibody is provided in an egg preparation from an avian.

4. The method of claim 2, wherein the antibody is administered orally.

5. The method of claim 4, wherein the antibody is mixed with a feed or food.

6. The method of claim 1, wherein the agent is administered by an injection method selected from subcutaneous injection, intraperitoneal injection, intramuscular injection, and intravenous injection.

7. The method of claim 1, wherein the animal is an avian.

8. The method of claim 7, wherein the avian is selected from a chicken, a pheasant, a turkey and a duck.

9. The method of claim 1, wherein the animal is a mammal.

10. The method of claim 9, wherein the mammal is selected from a porcine, a bovine, an ovine, a caprine, a rodent and a human.

11. The method of claim 1, wherein the animal is a fish.

12. The method of claim 2, wherein the animal is an avian.

13. The method of claim 12, wherein the avian is selected from a chicken, a pheasant, a turkey and a duck.

14. The method of claim 2, wherein the animal is a mammal.

15. The method of claim 14, wherein the mammal is selected from a porcine, a bovine, an ovine, a caprine, a rodent and a human.

16. The method of claim 1, wherein the agent is administered orally.

17. The method of claim 1, wherein the agent comprises a member selected from (i) an antibody to the extracellular domain of TLR4 or CD14 and (ii) a soluble peptide that can compete with TLR4 or CD14 to form a complex with endotoxin wherein the soluble peptide comprises said extracellular domain of TLR4 or CD14.

* * * * *